United States Patent [19]

Stutz, Jr.

[11] Patent Number: 5,413,595
[45] Date of Patent: May 9, 1995

[54] LEAD RETENTION AND SEAL FOR IMPLANTABLE MEDICAL DEVICE

[75] Inventor: William H. Stutz, Jr., Eagle Rock, Calif.

[73] Assignee: Pacesetter, Inc., Sylmar, Calif.

[21] Appl. No.: 137,648

[22] Filed: Oct. 15, 1993

[51] Int. Cl.$^6$ ............................................. A61N 1/372
[52] U.S. Cl. ..................................................... 607/637
[58] Field of Search ..................................... 607/36–38, 607/116

[56] References Cited

U.S. PATENT DOCUMENTS

| | | | |
|---|---|---|---|
| 3,760,332 | 9/1973 | Berkovits et al. | 607/37 X |
| 4,848,346 | 7/1989 | Crawford | 607/37 |
| 4,860,750 | 8/1989 | Frey et al. | |

Primary Examiner—Lee S. Cohen
Assistant Examiner—Jeffrey R. Jastrzab
Attorney, Agent, or Firm—Malcolm J. Romano; Lisa P. Weinberg

[57] ABSTRACT

A lead connector seal and locking assembly for an implantable pulse generator such as a pacemaker is detailed. The pulse generator includes a header portion and an enclosed metallic housing or can, wherein the header portion includes an orifice for receiving a lead connector. The lead connector is secured within the orifice by the use of a defeasible active seal and locking mechanism, which includes a sphincter seal and a beveled washer which is forced against the sphincter seal upon insertion of an actuator. The actuator may be a forked clip inserted into a slot formed within the epoxy header in such a manner that prongs of the forked clip force the beveled cam to be displaced axially within the orifice of the header portion, compressing the sphincter seal. The compression of the sphincter seal causes the sphincter seal to bulge radially, both outward and inward, in a generally symmetrical manner, thereby simultaneously contacting and sealing against the inside wall of the orifice of the header portion, and the body of the connector.

27 Claims, 4 Drawing Sheets

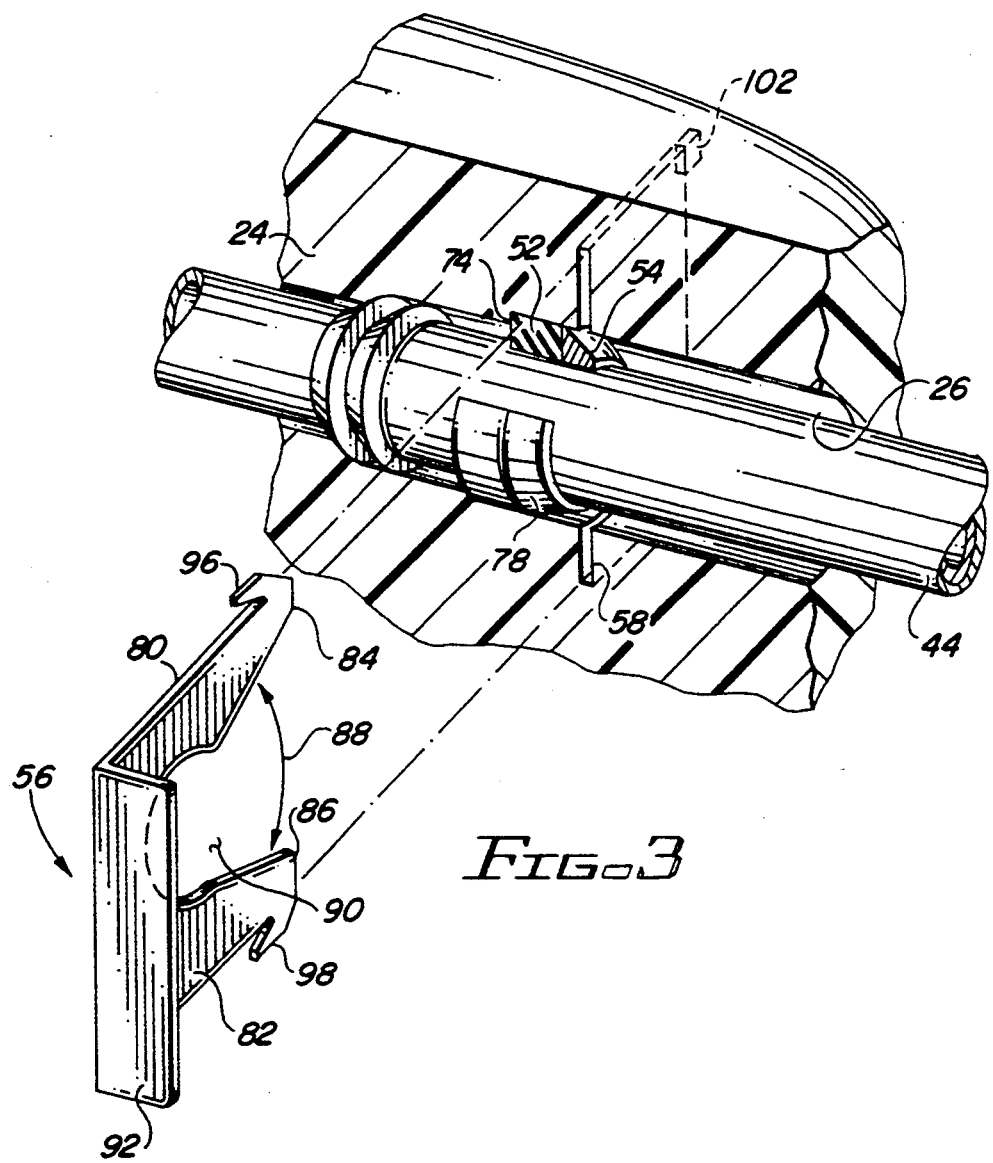
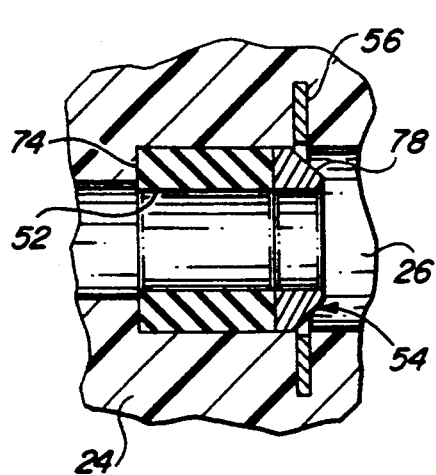
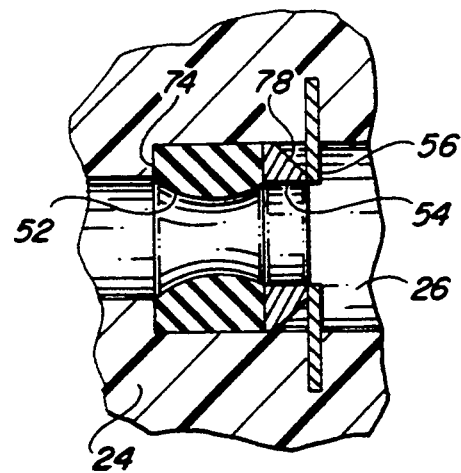

LEAD RETENTION AND SEAL FOR IMPLANTABLE MEDICAL DEVICE

FIELD OF THE INVENTION

The invention relates to implanted medical devices and connectors for coupling a lead, such as a cardiac pacing lead, to an implanted pulse generator and, more particularly, to a locking mechanical connector which prevents inadvertent decoupling of the lead from the pulse generator.

BACKGROUND OF THE INVENTION

Implantable electronic devices are in use providing electronic pulses to stimulate tissue via a lead extending from an implanted pulse generator to a desired internal location. An example of this type of technology is a pacemaker and a pacing lead which provides electrical stimulation to the heart. The pacemaker is usually implanted in a subcutaneous cavity, and the leads extend either transvenously to the internal cavities of the heart, or to patch electrodes located on external surface of the heart.

The leads generally include at least one electrode located at a distal end and an electrical connector for interconnection to the pulse generator at the proximal end. The connector at the proximal end and the distal electrode are interconnected by at least one conductor extending through an insulated body. It is common for the leads to include two or more electrodes and two or more electrical contacts at the connector.

The connector is inserted into a receiving orifice in a header portion of the pulse generator. The header portion of the pulse generator defining the receiving orifice may be formed from an epoxy material which is assembled and bonded to the main body of the pulse generator. The main body of the pulse generator is generally a metallic self-contained housing or can, which encloses the source of electrical energy and electrical circuitry for controlling the electrical stimulus delivered by the lead.

An alternative to the epoxy header design is discussed in detail in Truex et al. U.S. Pat. No. 4,934,366, which also teaches locking mechanism for securing the lead. The Truex et al. patent is assigned to the assignee of the present invention and is herein incorporated by reference.

Electrical contact elements, such as toroidal springs, are mounted in the header to make electrical contact with the electrical contacts of the lead connector, and feed the pulses to the body from the pulse generator. Generally, the electrical elements in the header are passive, in that they rely on deformation to maintain contact with the electrical contacts of the connector.

In the design of the lead connector and the pulse generator, it is important for the lead to be safely secured to the pulse generator to prevent inadvertent decoupling. In addition fluids must be prevented from invading the connection and contacting the electrical contacts. Generally, passive seals such as O-rings or circumferential ridges on the connector have been relied upon to passively prevent the invasion of fluids. However, these types of passive seals are quite delicate and tend to take a "set" over time and can possibly permit the invasion of body fluids.

It is also required that the insertion force for the connector be maintained below a fixed standard. Preferably, the force required to insert the connector into the pulse generator should be minimized. There are ISO industry standards for the maximum allowable insertion force of leads. The cumulative forces of the lead connector engaging passive elastic seals and spring-type contacts on the header connector can exceed these force limits.

It is also required that the interconnection between the pulse generator and the lead be defeasible, because the pulse generator must be capable of being removed while the lead will remain in place to be used with a new pulse generator. Accordingly, a mechanism for securing the connector in the pulse generator is required which will allow the lead connector to be removed from the pulse generator after many years without damage to the lead.

Various techniques have been used to actively secure the connectors to the pulse generator, for example, by the use of a set screw. Frey et al. U.S. Pat. No. 4,860,750 details a lead and pulse generator having a lead locking mechanism which includes a wedge member which interengages the lead to deform the lead and prevent disconnection. The wedge is inserted into a generally tangential slot in the header, and forces the lead to be deformed off center during insertion of the wedge. The lead may remain slightly compressed due to the shape of the wedge in a design according to Frey et al.

While Frey et al. is successful in securing the connector to the pulse generator, it has the undesirable effects of displacing the passive seals or O-rings, and also deforming the lead body. When the locking mechanism of Frey et al. is inserted, the lead body is displaced from axial alignment in the receiving orifice. This displacement causes the passive seals encircling the lead body to be compressed on one side, and potentially disengage or lose some of their delicate, passive loading from the opposite side, thereby opening a path for fluids to leak past the passive seal. In addition, most leads contain a helical wound conductor. Deformation of the lead body caused by the locking mechanism may result in crushing or flattening of the helical conductor, possibly leading to breakage.

Accordingly, it would be beneficial to have a pulse generator and lead assembly including an easily defeasible retention device which includes an alternative to the passive seals of the prior art, which has a minimum insertion force, and which secures the lead connector without damaging the conductors therein.

SUMMARY OF THE INVENTION

The present invention is directed to a pulse generator having a header portion and an enclosed metallic housing or can, wherein the header portion includes an orifice for receiving a lead connector. The lead connector is secured within the orifice by the use of a defeasible active seal and locking mechanism, which includes a sphincter seal and a beveled washer which is forced against the sphincter seal upon insertion of a forked clip. The forked clip is inserted into a slot formed within the epoxy header in such a manner that prongs of the forked clip force the beveled washer to be displaced axially within the orifice of the header portion, axially compressing the sphincter seal.

The axial compression of the sphincter seal causes the sphincter seal to bulge radially, both outward and inward, in a generally symmetrical manner, thereby simultaneously contacting and sealing against the inside wall of the orifice of the header portion, and the body of the lead connector. The sphincter seal is designed to securely clamp against the smooth cylindrical surface of the lead connector. However, upon removal of the forked clip, the sphincter seal expands axially and retracts radially, allowing for easy removal of the lead connector from the orifice.

An alternative embodiment includes the above sphincter seal combined with a sphincter actuated electrical contact element. The sphincter actuated electrical contact element includes a sphincter cylinder positioned about a conductive sleeve which is located so as to contact an electrical contact of the lead connector upon its insertion. The sphincter cylinder is also actuated by the insertion of the forked clip and displacement of the beveled washer, via a sleeve mounted between the sphincter seal and the sphincter cylinder. The compression of the sphincter cylinder forces the conductive sleeve into contact with the electrical contact of the lead connector, enhancing the electrical interconnection.

BRIEF DESCRIPTION OF THE DRAWINGS

FIG. 3 depicts a partial perspective cross-sectional view of the seal system of FIGS. 1 and 2 with the forked clip removed;

FIG. 4 depicts a partial cross-sectional view of the sphincter seal, beveled washer and forked clip, in an "open" position;

FIG. 5 depicts a partial cross-sectional view similar to FIG. 4, with the sphincter seal in the "closed" position;

DETAILED DESCRIPTION OF THE PREFERRED EMBODIMENTS

Figure 1:
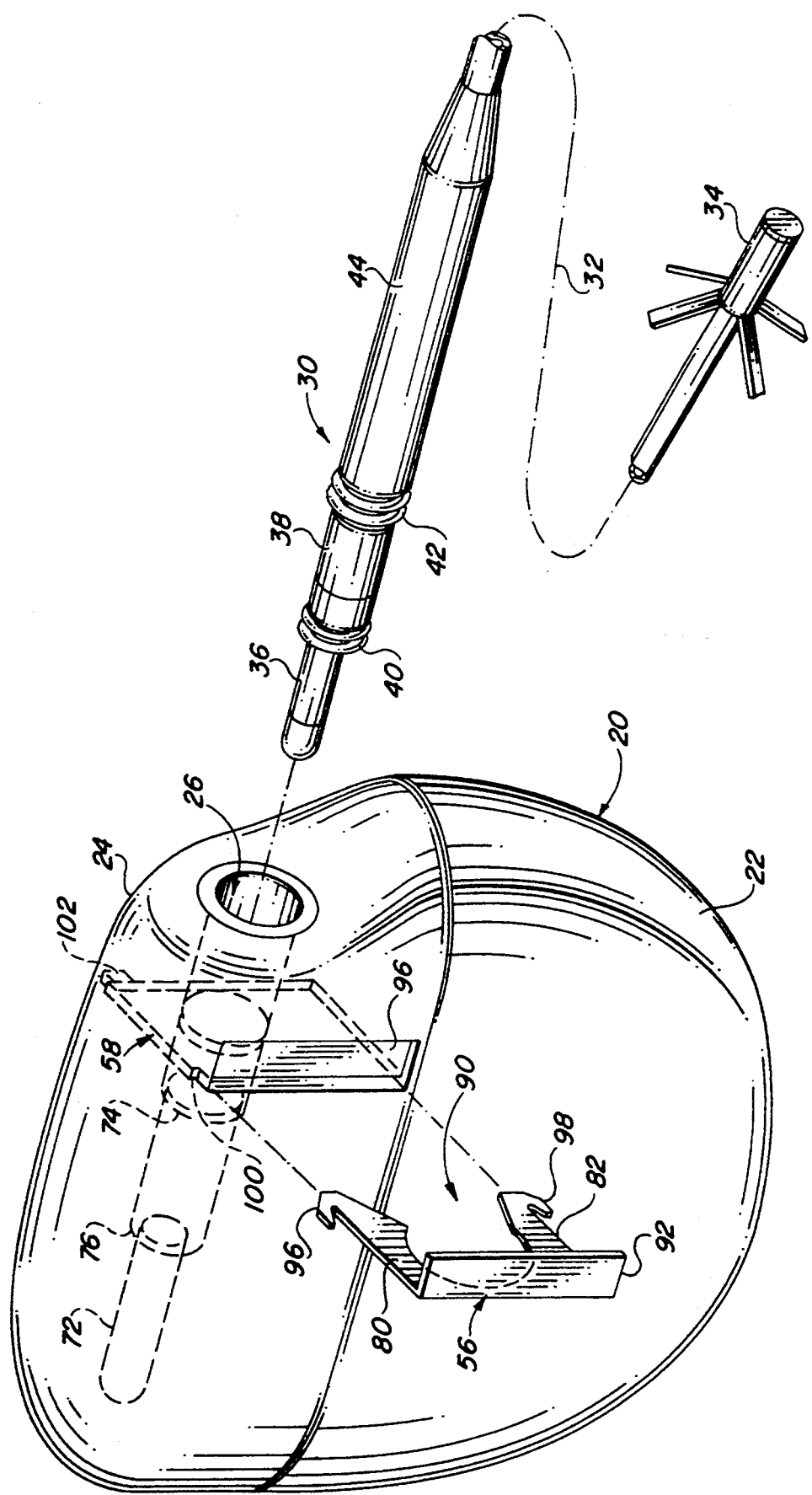
FIG. 1 depicts perspective view of the components of the system including the pulse generator, lead connector, and seal assembly.
Figure 2:
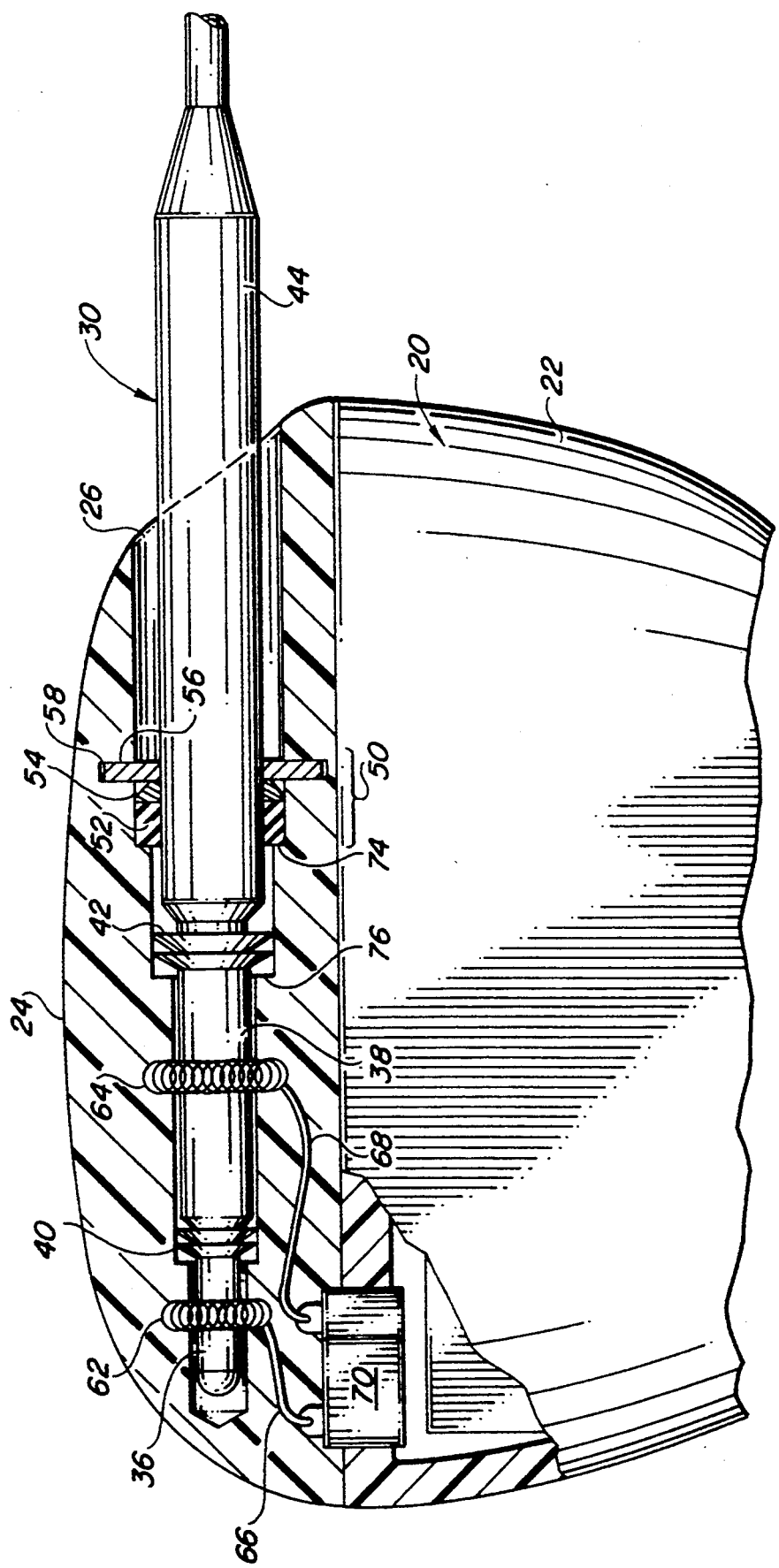
FIG. 2 depicts a partially cross-sectional view of the pulse generator and seal system with the lead connector inserted.

FIGS. 1-2 depict an implantable medical device including a pulse generator 20 such as a pacemaker, which includes a hermetically sealed metallic housing 22 containing a power supply and electronic components (not shown) of the pulse generator 20, and an attached header 24 including at least one connector receiving orifice 26. The header 24 may be either integral with the housing 22, or formed as a separate element and attached to the housing 22. Generally, when the header 24 is formed as a separate element as illustrated in the FIGS. 1-2, it is formed from an epoxy material.

Also depicted in FIGS. 1-2 is a lead connector assembly 30 of a lead 32, which is designed to be inserted into the orifice 26 of the header 24. The lead 32 also includes at least one electrode 34 at a distal end which is designed to deliver electrical stimulus from the pulse generator 20 to tissue. The lead connector assembly 30 includes a pair of electrical contacts 36 and 38, one of which may be a pin connector and the other may be a ring connector, as well as seals 40 and 42, and a lead boot 44.

FIGS. 1-5 illustrate the sphincter seal assembly 50 which includes a sphincter seal 52 and beveled washer 54 contained within the orifice 26 of header 24 and forked clip 56 which fits into a slot 58 formed in the header 24 transverse to the axis of orifice 26 to bisect a portion of the cylinder defining orifice 26. As depicted in FIG. 2, embedded within the epoxy header 24 are spring contacts 62 and 64 which are connected by wires 66 and 68, respectively, to a feedthrough 70. Upon insertion of the lead connector assembly 30 into the orifice 26, spring contact 62 completes an electrical connection to contact 36, while spring contact 64 will complete an electrical connection to contact 38 of the lead connector assembly 30.

As illustrated in FIG. 2, the orifice 26 is generally defined by a stepped bore 72. The stepped bore 72 generally includes one or more steps 74, 76, which transition to reduced diameters proceeding axially inward into the header 24. For the design of FIG. 2, the sphincter seal 52 has one end face abutting the step 74 within the stepped bore 72, and is thereby constrained from moving axially, i.e., further into the orifice 26.

In FIG. 3, the lead connector assembly 30 is depicted fully inserted into the orifice 26, prior to insertion of the forked clip 56 into slot 58. Accordingly, the sphincter seal 52 is in a relaxed state and a beveled surface 78 of beveled washer 54 projects into the slot 58.

The forked clip 56 shown in FIGS. 1 and 3 includes two prongs 80 and 82, which converge at an angle radially inward from their distal tips 84, 86 to define an opening 88. The converging surfaces of the opposing prongs 80 and 82 of the forked clip 56 converge to a minimum separation slightly greater than the diameter of the lead boot 44. The prongs 80 and 82 also preferably define a generally part-circular cutout 90, which has a diameter slightly greater than the diameter of the lead boot 44. Upon full insertion of the forked clip 56, the beveled washer 54 may spring back axially, to be seated against the cutout 90, to retain the forked clip 56 in a "closed" position. Accordingly, the forked clip 56 does not contact the lead boot 44, or retain the connection assembly 36 in the header 22 by direct engagement of the lead boot 44.

By the above design of the forked clip 56, upon initial insertion into slot 58, the inner surfaces of the respective prongs 80 and 82 will contact the largest diameter of the beveled surface 78 of the beveled washer 54. As the forked clip is inserted, the converging faces of the prongs 80 and 82 will progress down the beveled surface 78 of the beveled washer 54, forcing the beveled washer 54 axially toward the sphincter seal 52. The compressive force exerted by the moving beveled washer 54 on one side, and the stationary step 74 on the opposite side, causes sphincter seal 52 to expand radially, whereupon it seals against the surface of the lead boot 44.

The beveled washer 54 and the forked clip 56 are formed from a rigid biocompatible material, and the sphincter seal 52 is formed from a resilient biocompatible material capable of returning to an original shape upon release of pressure even after prolonged exposure to the intended implanted environment. Suitable materials for the beveled washer 54 and forked clip 56 include polysulfone plastic, stainless steel, or titanium, while the sphincter seal 52 is preferably formed from platinum cured silicone rubber or polyurethane, or similar materials.

The views of FIGS. 4 and 5 depict cross-sectional views of the sphincter seal assembly 50 in the "open" position and "closed" position, respectively, i.e. prior to and following insertion of the forked clip 56, without the lead boot 44 being inserted. As illustrated in FIG. 5, in the absence of the lead boot 44, the sphincter seal 52 will expand radially inward upon insertion of the forked clip 56, thereby being capable of exerting a substantial gripping force on the surface of the lead boot 44. Due to the uniform face loading which is exerted by the beveled washer 54 on the sphincter seal 52, the sphincter seal 52 expands uniformly, thereby exerting a uniform circumferential compressive load on the lead boot 44.

By the cooperative design of the sphincter seal 52 and the beveled washer 54 with the forked clip 56, the sphincter seal 52 will operate to actively retain the lead connector assembly 30 within orifice 26 of header 24, and additionally the sphincter seal 52 will act as a seal against the invasion of body fluids.

The forked clip 56 also preferably includes a tab 92, located at the end opposite that of the prongs 80 and 82. The tab 92 is designed to either lay against the outer surface of the header 24, or may be received within a shallow depression 94 formed therein, as shown in FIG. 1. Further, the tab 92 allows the physician the ability to grasp the forked clip 56 during insertion, and for removal, if necessary.

The forked clip 56 may also include barbs 96, 98 located at the proximal tips 84, 86 of the prongs 80, 82, respectively. The barbs 96, 98 are designed to engage a step 100 (FIG. 1) formed in the slot 58, upon insertion of the forked clip 56 into the slot 58. During initial insertion of the forked clip 56 into the slot 58, the prongs 80, 82 of the forked clip 56 will converge or bend inward to allow the barbs 96, 98 to pass within the walls of the slot 58. However, once the forked clip 56 is inserted into the slot 58 to the "open" position, the barbs 96, 98 will prevent the forked clip 56 from being fully removed from the slot 58 by engaging step 100. In addition, the header 24 may be designed to include a port 102 (FIG. 1) opening into the slot 58, to allow the insertion of a tool or implement (not shown) in order to force the forked clip 56 from the "closed" position into the "open" position.

Figure 6:
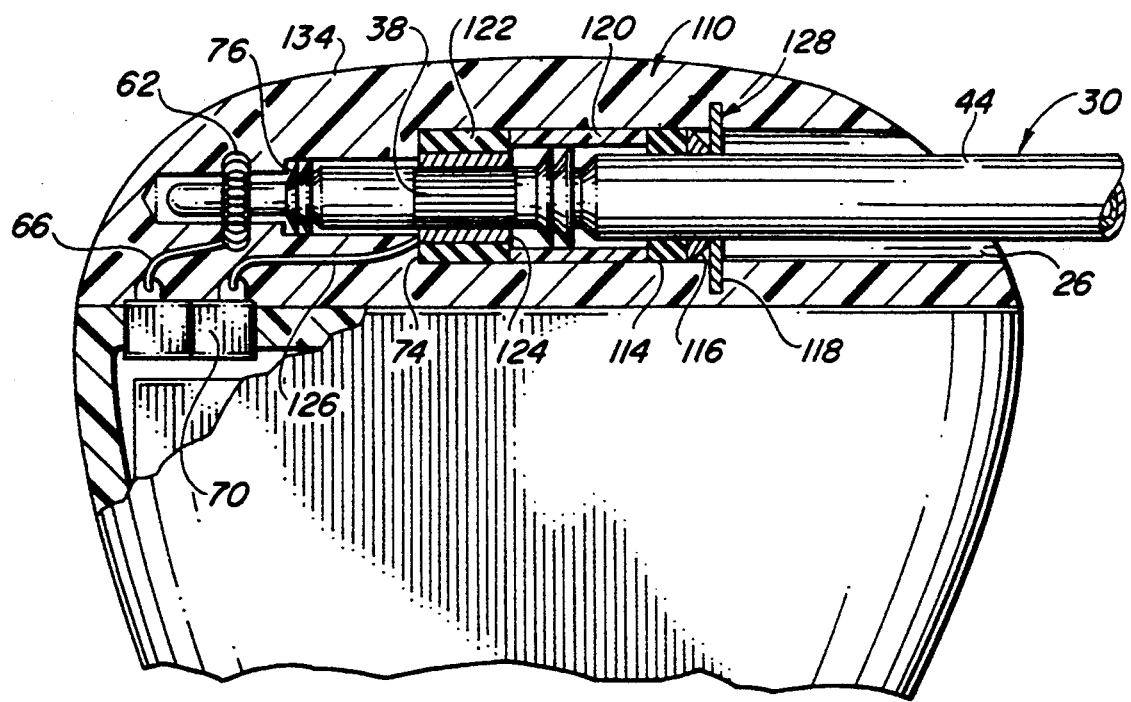
FIGS. 6 depicts a view similar to FIG. 2 for a first alternative embodiment having a sphincter seal and a sphincter actuated electrical connector.
Figure 7:
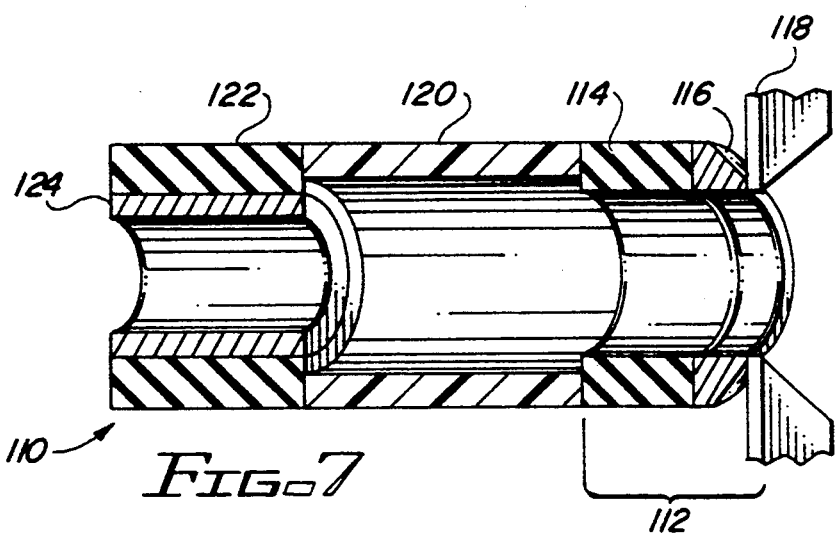
FIG. 7 depicts a partial perspective cross-sectional view of the alternative embodiment of FIG. 6.
Figure 8:
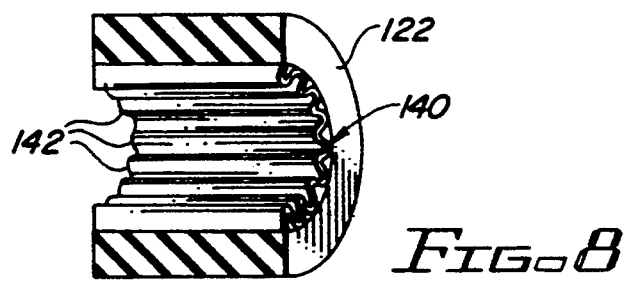
FIG. 8 depicts a partial view of an alternative sphincter actuated electrical connector which may be incorporated into the design of FIGS. 6 and 7.

Alternative embodiments of the present invention may be designed according to FIGS. 6-8. In FIG. 6, an assembled cross-sectional view of a combination sphincter seal and sphincter actuated electrical contact assembly 110, is illustrated. FIG. 7 depicts a partial perspective, cross-sectional view of the alternative embodiment of FIG. 6 removed from the orifice 26 of header 134. In FIGS. 6 and 7 the elements of the lead connector assembly 30 are identical to those described above, and the same numbers are included in the drawings of FIGS. 6 and 7 for reference. In addition, the spring contact 62, wire 66, feedthrough 70 and step 76 are identical to the like numbered elements in FIGS. 1-2 described above.

The assembly 110 of FIGS. 6 and 7 includes a sphincter assembly 112, generally according to FIGS. 1-3. Thus the sphincter assembly 112 includes a sphincter seal 114, a beveled washer 116 and a forked clip 118. The assembly 110 also includes a sliding sleeve 120 placed against one end of a sphincter element 122, the opposite end of the sphincter element abutting against the step 74 in the orifice 26. The sphincter element 122 is disposed about an electrical contact 124. The electrical contact 124 is interconnected via a wire 126 to the feedthrough 70.

Upon insertion of the forked clip 118 into a slot 128 in header 134, the beveled washer 116 is displaced axially to the left in FIG. 6, against the sphincter seal 114. The sphincter seal 114 is designed to be compressed between the sliding sleeve 120 and the beveled washer 116 so that the sphincter seal 114 bulges inward to seal against and secure the lead connector assembly 30 of the lead 32, as detailed above with respect to FIGS. 1-4. However, the sphincter seal 114 also forces the sliding sleeve 120 to move axially, thereby compressing the sphincter element 122 against step 74. The compression of the sphincter element 122 results in a bulging of the sphincter element 122, which forces the resilient electrical contact 124 radially inward, to securely press the electrical contact 124 into engagement with the contact 38 of the lead connector assembly 30.

In FIGS. 6 and 7, the resilient electrical contact 124 is illustrated as being a generally cylindrical element, having a smooth inner wall for engagement with the contact 38. Alternatively, as illustrated in FIG. 8, an electrical connector 140, designed to have axial corrugations 142, can be incorporated in the assembly 110 replacing electrical contact 124 within sphincter element 122. By this construction, the electrical connector 140 will have multiple points of engagement with a contact 38 of the lead connector assembly 30 (FIG. 6).

In the alternative embodiments of FIGS. 6-8, the sphincter seal 114 and the sphincter element 122 are preferably formed from a resilient elastomeric material such as platinum cured silicone rubber or polyurethane. By comparison, the forked clip 118, beveled washer 116, and rigid sleeve 120 are formed from a rigid biocompatible material, preferably polysulfone plastic, stainless steel, or titanium.

The embodiments of FIGS. 1-8 may be designed so that there will be zero insertion force required to insert the lead body into the sphincter seal when the forked clip is in the "open" position. In addition, the designs of FIGS. 6-8 may be configured so that there will be zero insertion force required for the sphincter actuated electrical connector.

It should be evident from the foregoing description that the present invention provides advantages over connector seals and locking mechanisms of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. An implantable medical device for delivering an electrical stimulus to tissue via an attached lead having a connector at a proximal end, the medical device comprising:
   pulse generating means for generating the electrical stimulus;
   a housing containing said pulse generating means, said housing including a header portion having at least one orifice for receiving the connector of the lead;
   sphincter seal means, disposed in said at least one orifice of said header portion of said housing, for sealing against intrusion of bodily fluids and locking in place the connector of the lead upon actuation into a closed position, and defeasibly unlocking the connector in said at least one orifice when said sphincter seal means is in an open position;

a slot formed in said header portion of said housing, said slot intersecting said at least one orifice in an area proximate said sphincter seal means disposed in said at least one orifice; and means for actuating said sphincter seal means between said open position and said closed position, said sphincter seal means being radially retracted about the connector when in said open position and radially expanded about the connector when in said closed position, said means for actuating being movable within said slot.

2. The implantable medical device of claim 1, wherein said means for actuating comprises:

a forked clip having a pair of prongs movable in said slot.

3. The implantable medical device of claim 1, wherein said sphincter seal means comprises:

a resilient sphincter seal formed from a biocompatible elastomeric material in the shape of an annular ring;

a beveled washer having an inner and an outer diameter, the beveled washer further having a first generally flat face abutting said sphincter seal and an opposing beveled face tapering from the outer diameter to the inner diameter to define a section of a cone; and a radial step formed in said at least one orifice, said resilient sphincter seal being positioned between said radial step and said beveled washer.

4. The implantable medical device of claim 3, wherein said means for actuating comprises:

a forked clip having a pair of prongs movable in said slot for engaging the beveled face of said beveled washer.

5. The implantable medical device of claim 4, wherein said forked clip and said beveled washer are formed from a rigid biocompatible material.

6. The implantable medical device of claim 5, wherein said rigid biocompatible material of said forked clip and said beveled washer is selected from the group consisting of polysulfone plastic, stainless steel, and titanium.

7. The implantable medical device of claim 4, further comprising:

means for retaining said forked clip in said slot following insertion, and for allowing said forked clip to be displaced in said slot so that said sphincter seal means is actuated between the open and the closed positions.

8. The implantable medical device of claim 3, wherein said resilient sphincter seal is formed from a resilient biocompatible material capable of returning to an original shape upon release of pressure even after prolonged exposure.

9. The implantable medical device of claim 8, wherein said resilient sphincter seal is formed from platinum cured silicone rubber.

10. The implantable medical device of claim 8, wherein said resilient sphincter seal is formed from polyurethane.

11. The implantable medical device of claim 1, wherein said housing includes a sealed metallic can and said header portion of said housing is formed from an epoxy material attached to said metallic can.

12. An implantable medical device for delivering an electrical stimulus via a defeasibly attached lead having a connector at a proximal end, the implantable medical device comprising:

pulse generating means for generating the electrical stimulus;

a sealed housing containing said pulse generating means;

a header affixed to the sealed housing, said header including at least one orifice for receiving the connector of the lead; and connector locking means, disposed in said at least one orifice of said header, for providing a seal which has a predetermined amount of insertion force between an inner wall of said at least one orifice and an outer surface of the connector when said locking means is in an unlocked position, and for providing a seal with a circumferential, gripping force when the locking means is in a locked position, whereby said connector locking means firmly holds the proximal end of the connector in place while preventing the intrusion of bodily fluids.

13. The implantable medical device of claim 12, wherein said connector locking means comprises:

a sphincter seal disposed in said at least one orifice of said header for sealing against and locking in place the connector of the lead upon actuation into a closed position and defeasibly unlocking the connector in said at least one orifice in an open position; and means for actuating said sphincter seal from said open position to said closed position.

14. The implantable medical device of claim 13, wherein said sphincter seal means comprises:

a resilient sphincter seal formed from a biocompatible elastomeric material;

a beveled washer having an inner and an outer diameter, the beveled washer further having a first generally flat face abutting said sphincter seal and an opposing beveled face tapering from the outer diameter to the inner diameter to define a section of a cone; and a radial step formed in said at least one orifice, said resilient sphincter seal being positioned between said radial step and said beveled washer.

15. The implantable medical device of claim 14, wherein said means for actuating comprises:

a slot formed in said header, said slot intersecting said at least one orifice in an area proximate said beveled washer of said sphincter seal; and a forked clip having a pair of prongs movable in said slot for engaging the beveled face of said beveled washer.

16. The implantable medical device of claim 15, wherein said forked clip and said beveled washer are formed from a rigid biocompatible material selected from the group consisting of polysulfone plastic, stainless steel, and titanium, and wherein said resilient sphincter seal is formed from a material selected from the group consisting of platinum cured silicone rubber and polyurethane.

17. The implantable medical device of claim 12, wherein said predetermined amount of insertion force comprises a zero insertion force.

18. An implantable medical device for delivering an electrical stimulus to tissue via a lead having a connector including an electrical contact at a proximal end, the medical device comprising:

pulse generating means for generating the electrical stimulus;

a sealed housing containing said pulse generating means;

a header affixed to said sealed housing, said header including at least one orifice for receiving the connector of the lead;

sphincter seal means, disposed in said at least one orifice of said header, for sealing against intrusion of bodily fluids and locking in place the proximal end of the connector of the lead upon actuation into a closed position, and for defeasibly unlocking the connector in said at least one orifice when said sphincter seal means is in an open position;

sphincter actuated electrical contact means for constricting about the electrical contact of the connector; and means for actuating said sphincter seal means between said open position and said closed position, said sphincter seal means being radially retracted about the connector when in said open position and radially expanded about the connector when in said closed position, and for actuating said sphincter actuated electrical contact means.

19. The implantable medical device of claim 18, wherein said sphincter seal means and said sphincter actuated electrical contact means comprise:

a sphincter seal formed from a resilient biocompatible material;

a beveled washer having an inner and an outer diameter, the beveled washer further having a first generally flat face abutting said sphincter seal and an opposing beveled face tapering from the outer diameter to the inner diameter to define a cone;

a generally cylindrical sphincter element formed from a resilient biocompatible material;

an electrical contact element disposed within said generally cylindrical sphincter element;

a rigid sleeve positioned between and axially spacing said sphincter seal and said generally cylindrical sphincter element; and a radial step formed in said at least one orifice, said generally cylindrical sphincter element having an end face abutting said radial step.

20. The implantable medical device of claim 19, wherein said means for actuating comprises:

a slot formed in said header, said slot intersecting said at least one orifice of said header in an area proximate said beveled washer; and a forked clip having a pair of prongs movable in said slot against the beveled face of said beveled washer to displace said beveled washer axially toward said sphincter seal, causing compression of both said sphincter seal and said generally cylindrical sphincter element.

21. The implantable medical device of claim 20, wherein said sphincter seal and said sphincter element are formed from a resilient biocompatible material selected from the group consisting of platinum cured silicone rubber and polyurethane.

22. The implantable medical device of claim 21, wherein said electrical contact element disposed within said generally cylindrical sphincter element is a generally cylindrical metallic material.

23. The implantable medical device of claim 22, wherein said electrical contact element includes axially aligned corrugations.

24. The implantable medical device of claim 20, wherein said forked clip, said beveled washer, and said rigid sleeve are formed from a rigid biocompatible material selected from the group consisting of polysulfone plastic, stainless steel, and titanium.

25. A implantable stimulation device for delivering stimulation pulses to the heart via an attached lead having a connector at a proximal end, comprising:

pulse generating means for generating the stimulation pulses;

a housing containing said pulse generating means, said housing including a header having a channel for receiving the connector of the lead;

sphincter seal/locking means, disposed in said channel of said header, for actively sealing against intrusion of bodily fluids and locking in place the connector of the lead upon actuation into a closed position, and for defeasibly unlocking and unsealing the connector in said channel when said sphincter seal/locking means is in an open position; and means for actuating said sphincter seal/locking means between said open position and said closed position.

26. The implantable stimulation device of claim 25, wherein said sphincter seal/locking means comprises:

a resilient sphincter seal formed from a biocompatible elastomeric material in the shape of an annular ring.

27. The implantable stimulation device of claim 26, wherein said means for actuating comprises:

a beveled washer having an inner and an outer diameter, the beveled washer further having a first generally flat face abutting said resilient sphincter seal and an opposing beveled face tapering from the outer diameter to the inner diameter to define a section of a cone;

a radial step formed in said channel, said resilient sphincter seal being positioned between said radial step and said beveled washer;

a slot formed in said header, said slot intersecting said channel in an area proximate said resilient sphincter seal; and a forked clip having a pair of prongs movable in said slot;

whereby when said forked clip is inserted into said slot, said beveled washer becomes axially displaced and said resilient sphincter seal becomes radially expanded, thereby gripping the connector of the lead and further actively sealing against the intrusion of bodily fluids.

* * * * *